United States Patent [19]

Fryberg

[11] Patent Number: 4,568,752
[45] Date of Patent: Feb. 4, 1986

[54] RECORDING MATERIAL FOR COLOR PHOTOGRAPHY

[75] Inventor: Mario Fryberg, Praroman-le-Mouret, Switzerland

[73] Assignee: Ciba-Geigy AG, Basel, Switzerland

[21] Appl. No.: 680,403

[22] Filed: Dec. 10, 1984

Related U.S. Application Data

[60] Continuation of Ser. No. 453,567, Dec. 27, 1982, abandoned, which is a continuation of Ser. No. 121,861, Feb. 15, 1980, abandoned, which is a division of Ser. No. 47,465, Jun. 11, 1979, Pat. No. 4,238,564.

[30] Foreign Application Priority Data

Jun. 20, 1978 [CH] Switzerland .......................... 6730/78

[51] Int. Cl.$^4$ ............................ G03C 7/00; G03C 1/40
[52] U.S. Cl. ..................................... 548/139; 548/277; 548/264; 548/308; 548/268; 548/262; 546/256; 562/455; 564/80; 564/153
[58] Field of Search ............... 548/139, 227, 264, 308, 548/268, 262; 546/256; 562/455; 564/80, 153

[56] References Cited

U.S. PATENT DOCUMENTS 1,580,709  4/1926  Zitscher et al. ................ 564/153
4,115,121  9/1978  Evans et al. .................... 430/557
4,248,961  2/1981  Hagen et al. .................... 430/381

Primary Examiner—John Kight
Assistant Examiner—M. L. Moore
Attorney, Agent, or Firm—Joseph G. Kolodny

[57] ABSTRACT

Recording material for color photography, which contains, in at least one silver halide emulsion layer, at least one yellow coupler of the formula

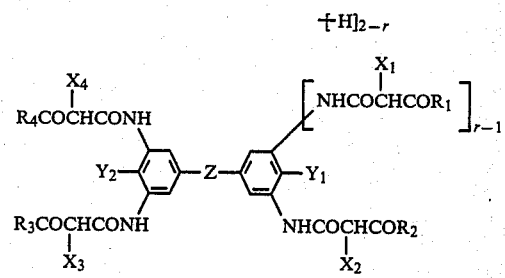

in which $R_1$, $R_2$, $R_3$ and $R_4$ are alkyl, cycloalkyl or aryl, $X_1$, $X_2$, $X_3$ and $X_4$ are radicals detachable during the coupling reaction and $Y_1$ and $Y_2$ are halogen, alkyl, alkoxy, alkylmercapto, —CN, —COOH, carbalkoxy, —NH$_2$, —NHR$_5$, —NR$_5$R$_6$ or —NHCOR$_5$, in which $R_5$ and $R_6$ are alkyl or phenyl, Z is a divalent bridge member and r is 1 or 2.

Photographic colored images with excellent spectral absorption characteristics and good resistance to light, heat and moisture are obtained by exposing the recording material image-wise and developing.

1 Claim, No Drawings

RECORDING MATERIAL FOR COLOR PHOTOGRAPHY

This is a continuation of application Ser. No. 453,567 filed Dec. 27, 1982, now abandoned which is cont of Ser. No. 121,861 filed 2/15/80 (now abandoned) which is divisional of Ser. No. 047,465 filed 6/11/79 now U.S. Pat. No. 4,238,564.

In order to produce coloured photographic images, exposed silver halide emulsion layers, which at the same time contain colour couplers, are, as is known, developed with a developer substance which contains aromatic primary amino groups. The oxidised developer substance reacts with the colour coupler with the formation of an image dye, the amount of the latter depending on the amount of silver developed.

In general, a light-sensitive photographic multilayer material is used which consists of a red-sensitive layer, which contains the cyan coupler, a green-sensitive layer, which contains the magenta coupler, and a blue-sensitive layer, which, in turn, contains the yellow coupler. On colour developing, the corresponding dyes having the colours cyan, magenta and yellow then form.

Usually, phenols or α-naphthols are employed as cyan couplers, pyrazolones are employed as magenta couplers and acylacetylamides are employed as yellow couplers. The dyes formed after developing are then indophenols, indamines or azomethines.

A structural characteristic of the conventional yellow couplers is an active methylene group, it being possible, in some cases, for one hydrogen atom to be replaced by a group which is detachable during the coupling reaction. In the first case, the couplers are termed four-equivalent couplers, since four equivalents of silver halide are required to form the image dye. In the second case, only two equivalents of silver halide are used to produce the corresponding image dye (two-equivalent couplers). These known couplers yield image dyes which each contain a chromogenic grouping (aziomethine grouping) and a ballast group. Although the ballast groups are of importance inasmuch as they are responsible, for example, on the one hand for the solubility of the couplers and on the other hand also for the resistance of the dyes to diffusion, they can, however, also have an adverse influence on the photographic characteristics of the recording material for colour photography (for example as a result of undesired light absorption); moreover, they make no contribution towards increasing the colour yield of the image dye to be formed. In order to overcome these disadvantages either the size of the ballast groups can be reduced (which, however, because of the demands made of these groups hardly promises success) or the number of chromogenic groupings per molecule is increased. As a result of this measure, the molar colour-forming capacity of the couplers is increased and a greater colour density is obtained, so that the amount of coupler employed can be reduced, by which means, at the same time, the quantity of ballast groups and, thus, their possible adverse influence on the photographic material can also be reduced. Colour couplers of this type are known, for example, from U.S. Pat. No. 3,077,403 and German Offenlegungsschrift 2,408,168. However, the characteristics of these couplers in use are still not entirely satisfactory.

The object of the present invention is, therefore, to provide novel materials for colour photography which have improved characteristics and in which compounds which contain, per molecule, three or four chromogenic groupings and one bridge member between the chromogenic groupings are employed as yellow couplers.

The colour couplers to be employed according to the invention can be either so-called 3×2- or 4×2-equivalent couplers or 3×4- or 4×4-equivalent couplers, i.e. compounds which contain, per molecule, 3 or 4 reactive positions which contain, per molecule, 3 or 4 reactive positions capable of forming a colour with the oxidised developer.

The present invention relates to a light-sensitive recording material for colour photography, which contains, in at least one silver halide emulsion layer, at least one yellow coupler of the formula

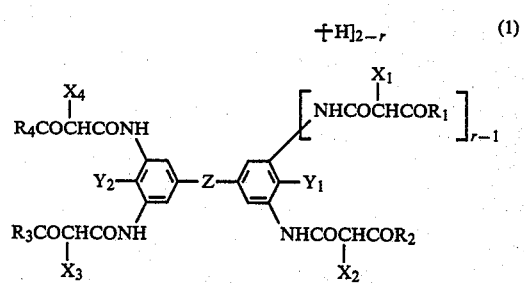

in which $R_1$, $R_2$, $R_3$ and $R_4$ are alkyl, cycloalkyl or aryl, $X_1$, $X_2$, $X_3$ and $X_4$ are radicals detachable during the coupling reaction and $Y_1$ and $Y_2$ are halogen, alkyl, alkoxy, alkylmercapto, —CN, —COOH, carbalkoxy, —$NH_2$, —$NHR_5$, —$NR_5R_6$ or —$NHCOR_5$, in which $R_5$ and $R_6$ are alkyl or phenyl, Z is a divalent bridge member and r is 1 or 2.

The invention also relates to a process for colour photography, for the production of a yellow image by colour developing an exposed recording material which contains at least one compound of the formula (1) as the yellow coupler, the compounds of the formula (1) and the use of compounds of the formula (1) as yellow couplers in light-sensitive recording materials for colour photography.

Suitable alkyl radicals $R_1$, $R_2$, $R_3$ and $R_4$ in compounds of the formula (1) can contain 1 to 18 carbon atoms and can be straight-chain or branched, for example methyl, ethyl, propyl, i-propyl, butyl, isobutyl, tert.-butyl, amyl, tert.-amyl (1,1-dimethylpropyl), 1,1,3,3-tetramethylbutyl, 1-methyl-1-ethylpentyl, hexyl, 1-methylpentyl, neopentyl, 1-, 2- or 3-methylhexyl, heptyl, n-octyl, tert.-octyl, 2-ethylhexyl, n-nonyl, isononyl, tert.-nonyl, decyl, tert.-decyl and undecyl; and also dodecyl, tetradecyl, hexadecyl and octadecyl and the corresponding isomers. Straight-chain or branched alkyl radicals having 3 to 10 carbon atoms are particularly suitable and amongst these tert.-alkyl radicals having 4 to 8 carbon atoms are preferred.

Tert.-butyl, 1,1,3,3-tetramethylbutyl, 1-methyl-1-ethylpentyl and 1,1-dimethylpropyl are particularly preferred tertiary alkyl radicals.

Cycloalkyl is, for example, cycloalkyl having 3 to 12 ring carbon atoms, for example cyclopropyl, cyclobutyl, cyclopentyl and cyclohexyl, and also cyclooctyl and cyclododecyl, which can be substituted. Cycloalkyl also includes bi- and tri-cycloalkyl, for example norbornyl and adamantyl. Cyclopentyl, cyclohexyl and adamantyl are preferred.

Aryl radicals are in particular phenyl or substituted phenyl, in which substituents (one or more substituents) can be halogen, for example fluorine, chlorine or bromine, or alkyl or alkoxy, preferably each having 1 to 4 carbon atoms, for example methyl, ethyl, propyl, i-propyl, butyl, tert.-butyl, methoxy, ethoxy, propoxy or butoxy, and also amino (—NH$_2$), sulfo (—SO$_3$H), alkylsulfonyl and acylamino; the latter two radicals can be represented by the formulae —SO$_2$R$_{11}$ and —NHCOR$_{12}$—, in which R$_{11}$ is alkyl having 1 to 5 carbon atoms, for example methyl, ethyl, propyl, i-propyl, butyl or amyl, and R$_{12}$ is likewise alkyl having 1 to 5 carbon atoms, specific radicals being the same as those mentioned for R$_{11}$. A further substituent on the phenyl ring can be —O(CH$_2$)$_r$O—, in which r is 1 or 2.

Phenyl substituted by halogen and alkyl or alkoxy each having 1 to 4 carbon atoms is preferred as the aryl radical.

The radicals R$_1$, R$_2$, R$_3$ and R$_4$ can be identical or different to one another.

As radicals detachable during the coupling reaction, X$_1$, X$_2$, X$_3$ and X$_4$, which can be identical or different to one another, can be hydrogen, halogen, alkoxy and phenoxy, substituted or unsubstituted, nitrogen-containing, 5-membered or 6-membered heterocyclic radicals, which are bonded to the coupling position via a nitrogen atom, the radicals —S—R$_{13}$ and —OPO(OR$_{14}$)$_2$, in which R$_{13}$ is alkyl, substituted phenyl or a heterocyclic radical and R$_{14}$ is alkyl or phenyl, as well as a radical of the formula

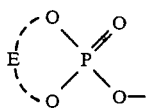

in which E is the remaining part of a radical containing the ring consisting of the phosphorus atom, the two oxygen atoms and 3 carbon atoms. Bromine and in particular chlorine are suitable as detachable halogen. The alkoxy radical can contain 1 to 4 carbon atoms and the phenoxy radical can be substituted by nitro, carboxyl or a carboxylic ester, in which the alcohol component of the ester can contain 1 to 4 carbon atoms. Specific examples of carboxylic ester substituents are methyl, ethyl, propyl and butyl ester groups.

The 5-membered or 6-membered heterocyclic radicals, which are bonded to the coupling position via a nitrogen atom, are, for example, heterocyclic radicals which contain one or more nitrogen, sulfur and/or oxygen atoms and can be fused with a further ring. Examples are the radicals of pyrazole, imidazole, triazoles (1,2,3 and 1,2,4), tetrazoles, benztriazole, pyrimidine, pyridazine, thiazole, oxazole and oxazine; and also cyclic imides. The said heterocyclic radicals can be in the unsubstituted or substituted form.

Attention is drawn to the following publications with regard to further details on leaving groups in two-equivalent yellow couplers;

Halogen atoms, as described, for example, in German Offenlegungsschrift 2,114,577, French Patent Specifications 991,453 and 869,169 or U.S. Pat. Nos. 2,728,658 and 3,277,155:

the group —OR, in which R is alkyl, aryl, a heterocyclic radical or acyl, as described, for example, in British Patent Specification 1,092,506, French Patent Specifications 1,411,385 and 1,385,696 or in U.S. Pat. Nos. 3,447,928 and 3,408,194;

the —SR"— group described in British Patent Specification 953,454 or U.S. Pat. No. 3,265,506;

the 1,2,3-benztriazolyl group of the formula

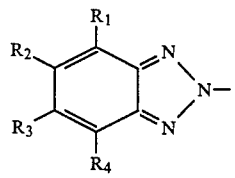

(German Offenlegungsschrift 1,800,420)
the radicals —SO$_3$H and —SCN (British Patent Specification 638,039; U.S. Pat. No. 3,253,924) imide groups of the formulae

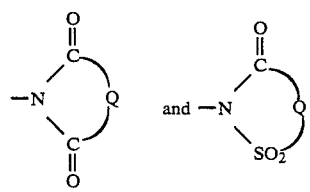

(German Offenlegungsschriften 2,163,812, 2,213,461 and 2,057,941);
radicals of the formula

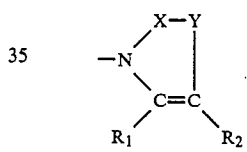

(German Offenlegungsschrift 2,329,587);
leaving groups of the formula

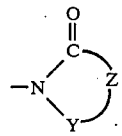

(German Offenlegungsschrift 2,433,812)
1,2,4-triazolyl- or 1,2,3-benzotriazinyl-4-(3)-one radicals as leaving groups (German Offenlegungsschrift 2,528,638);
1,2,4-triazolyl or tetrazolyl radicals as leaving groups (German Offenlegungsschrift 2,442,703)
open-chain or cyclic sulfonamidyl radicals as leaving groups (German Offenlegungsschrift 2,454,741);
leaving groups of the formula

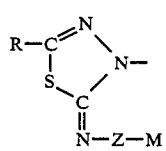

(German Offenlegungsschrift 2,716,204)
and leaving groups of the formula

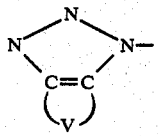

in which V together with the —C═C— grouping forms an aromatic ring of the benzene series or a heterocyclic ring containing at least one nitrogen atom (German Offenlegungsschrift 2,414,006).

The substituents $Y_1$ and $Y_2$, which can be identical or different to one another, can be halogen, for example fluorine, chlorine or bromine, or alkyl, alkoxy or alkylmercapto, each having preferably 1 to 12 carbon atoms, for example methyl, ethyl, propyl, butyl, amyl, hexyl, octyl, nonyl, decyl, undecyl or dodecyl, and the corresponding isomers, and also the analogous alkoxy or alkylmercapto radicals. Suitable substituents $Y_1$ and $Y_2$ are also —CN, —COOH, carbalkoxy having not more than 12 carbon atoms in the alkoxy moiety, —$NH_2$, alkylamino, phenylamino, dialkylamino and diphenylamino, in which alkyl preferably contains 1 to 5 carbon atoms, or acylamino, in which the acyl radical contains 2 to 13 carbon atoms and as a rule is derived from alkylcarboxylic acids with the corresponding number of carbon atoms or from benzoic acid ($C_6H_5COOH$).

Preferred radicals $Y_1$ and $Y_2$ are —$NHCOR_{15}$ radicals in which $R_{15}$ is alkyl having 1 to 12 carbon atoms or also in particular chlorine, or also methyl or methoxy.

The bridge member Z, which is located in the para-position relative to the substituents $Y_1$ and $Y_2$, can be substituted or unsubstituted alkylene or alkenylene and also cycloalkylene or a bridge member, which contains, as linking elements, amino, acyl and/or acylamino groups, in which acyl is derived from organic or inorganic oxy acids.

Z is, for example, straight-chain alkylene having 1 to 20 carbon atoms. Alkylene radicals Z can thus be: methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, nonadecylene and eicosylene.

The straight-chain alkylene bridge member can also be substituted by alkyl, hydroxyalkyl, alkoxyalkyl, aminoalkyl, acylaminoalkyl or halogenoalkyl (halogen: F, Cl or Br) having 1 to 10 carbon atoms in the alkyl moiety and 1 to 5 carbon atoms in the alkoxy and acyl moieties.

Further substituents can be hydroxyl (OH) or halogen (F, Cl or Br); alkoxy ($C_1$-$C_5$); amino ($NH_2$), N-alkyl- and N,N-dialkyl-amino, for example $CH_3NH$—, $C_5H_{11}NH$—,

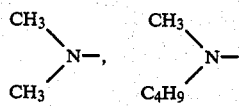

and the corresponding homologues.

Further substituents on straight-chain alkylene (Z) are mercapto (—SH) and alkylmercapto ($CH_3S$— or $C_5H_{11}S$—).

There can be one or more of the said substituents on the alkylene bridge member. Alkenylene Z can contain 2 to 20 and especially 2 to 10 carbon atoms and is, for example, ethenylene, propenylene, butenylene, pentenylene or decenylene. Cycloalkylene Z can contain 3 to 12 carbon atoms. The divalent radicals analogous to cycloalkyl, which have been mentioned for $R_1$ to $R_4$, are preferred.

Further bridge members (Z) are:

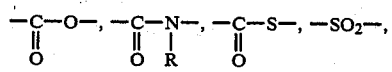

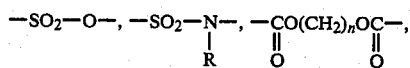

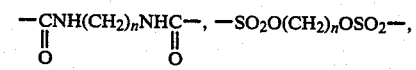

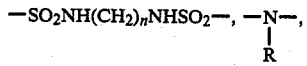

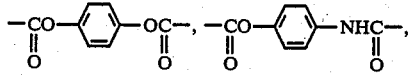

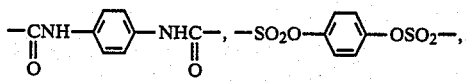

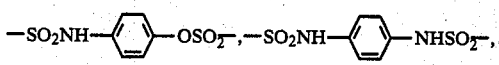

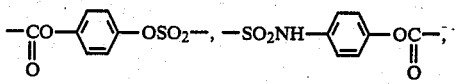

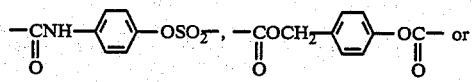

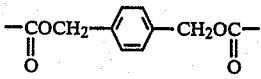

in which R is hydrogen or alkyl having 1 to 10 carbon atoms, which is unsubstituted or substituted by halogen, hydroxyl or acyl having 2 to 5 carbon atoms, and n is an integer from 2 to 20.

As alkyl having 1 to 10 carbon atoms, R can be, for example, methyl, ethyl, propyl, butyl, pentyl, hexyl, heptyl, octyl, nonyl, decyl, undecyl or dodecyl or a corresponding isomer (branched alkyl). The halogen substituents on alkyl are preferably fluorine, chlorine and bromine, whilst acyl is, for example, acetyl, propionyl, butanoyl or pentanoyl.

These bridge members are linked to the two phenyl rings in the manner indicated for the bridge members. The left/right arrangements, both in the formulae and in the bridge members, are thus to be left unchanged.

The formula (I) comprises yellow couplers of the formula

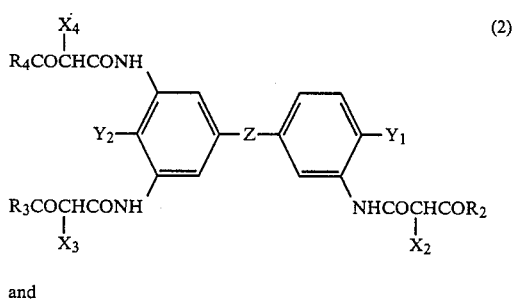

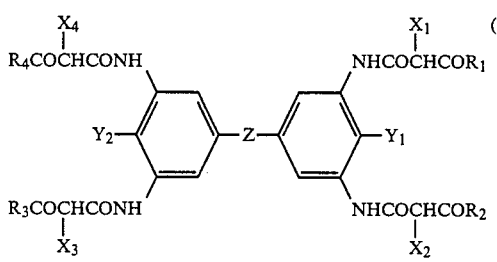

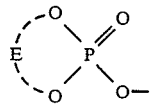

in which Z is as defined but is in particular straight-chain alkylene having 1 to 20 carbon atoms, which is unsubstituted or substituted by alkyl, hydroxyalkyl, alkoxyalkyl, aminoalkyl, acylaminoalkyl or halogenoalkyl, each having 1 to 10 carbon atoms in the alkyl moiety, hydroxyl, halogen, alkoxy having 1 to 5 carbon atoms, amino ($-NH_2$), N-alkylamino and N,N-dialkylamino, each having 1 to 5 carbon atoms in the alkyl moiety, mercapto ($-SH$) and/or alkylmercapto having 1 to 5 carbon atoms, or also cycloalkylene having 3 to 12 carbon atoms, and $R_1$, $R_2$, $R_3$, $R_4$, $X_1$, $X_2$, $X_3$, $X_4$, $Y_1$ and $Y_2$ are as defined.

Preferred recording material for colour photography is that which contains, as the yellow coupler, compounds of the formula

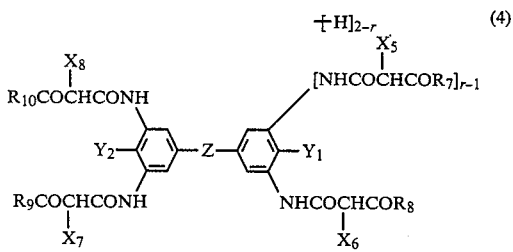

in which $R_7$, $R_8$, $R_9$ and $R_{10}$ are straight-chain or branched alkyl having 1 to 18 carbon atoms, cycloalkyl, bicycloalkyl or tricycloalkyl having 3 to 12 ring carbon atoms, phenyl or phenyl substituted by halogen, alkyl or alkoxy, each having 1 to 4 carbon atoms, or substituted by $-O(CH_2)_rO-$, $-NH_2$, $-SO_2R_{11}$ or $-NHCOR_{12}$, in which $R_{11}$ is alkyl having 1 to 5 carbon atoms and $R_{12}$ is alkyl having 1 to 5 carbon atoms, $X_5$, $X_6$, $X_7$ and $X_8$ are hydrogen, halogen, substituted or unsubstituted alkoxy or phenoxy, nitrogen-containing 5-membered or 6-membered heterocyclic radicals, which are bonded to the coupling position via a nitrogen atom, or $-S-R_{13}$ in which $R_{13}$ is alkyl, substituted phenyl or a heterocyclic radical, $-OPO(OR_{14})_2$, in which $R_{14}$ is alkyl or phenyl, or a radical of the formula

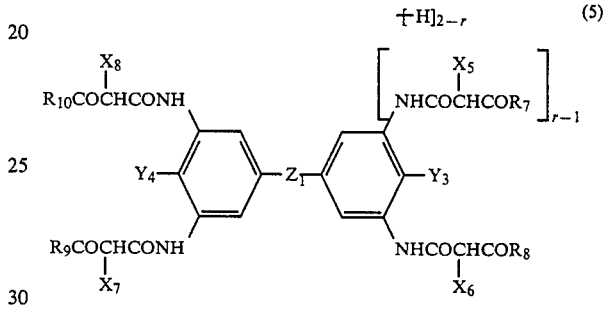

in which E is the remaining part of a radical containing the six-membered ring consisting of the phosphorus atom, the two oxygen atoms and 3 carbon atoms, $Y_1$ and $Y_2$ are halogen, alkyl, alkoxy, alkylmercapto, $-CN$, $-COOH$, carbalkoxy, $-NH_2$, $-NHR_5$, $-NR_5R_6$ or $NHCOR_5$, in which $R_5$ and $R_6$ are alkyl or phenyl, r is 1 or 2 and Z is as defined.

Particularly suitable recording materials are also those which contain the yellow couplers of the formula

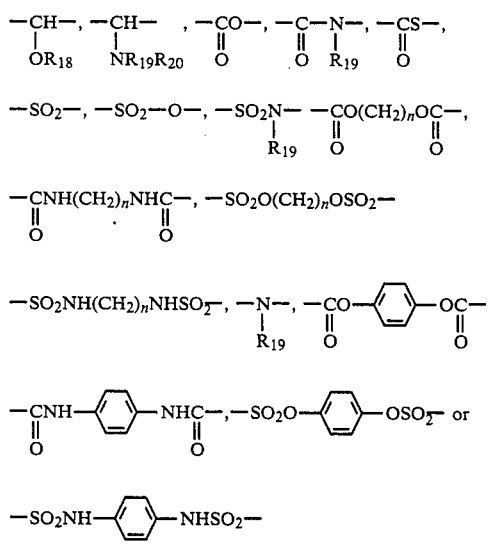

in which $Y_3$ and $Y_4$ are fluorine, chlorine, bromine, alkyl, alkoxy and alkylmercapto, each having 1 to 12 carbon atoms, $-CN$, $-COOH$, $-COOR_{15}$, $-NH_2$, $-NHR_{16}$, $-NR_{16}R_{17}$ or $-NHCOR_{15}$, in which $R_{16}$ and $R_{17}$ are alkyl having 1 to 5 carbon atoms or phenyl and $R_{15}$ is alkyl having 1 to 12 carbon atoms or phenyl, $Z_1$ is $-(CH_2)_m-$, which is unsubstituted or substituted by alkyl, hydroxyalkyl, alkoxyalkyl, aminoalkyl and/or halogenoalkyl, each having 1 to 5 carbon atoms in the alkyl and alkoxy moieties, and $Z_1$ is also $$-\underset{\underset{OR_{18}}{|}}{CH}-,\ -\underset{\underset{NR_{19}R_{20}}{|}}{CH}-,\ -\underset{\underset{O}{||}}{C}O-,\ -\underset{\underset{O}{||}}{C}-\underset{\underset{R_{19}}{|}}{N}-,\ -\underset{\underset{O}{||}}{C}S-,$$

$$-SO_2-,\ -SO_2-O-,\ -\underset{\underset{R_{19}}{|}}{SO_2N}-\ -\underset{\underset{O}{||}}{C}O(CH_2)_n\underset{\underset{O}{||}}{O}C-,$$

$$-\underset{\underset{O}{||}}{C}NH(CH_2)_n\underset{\underset{O}{||}}{N}HC-,\ -SO_2O(CH_2)_nOSO_2-$$

$$-SO_2NH(CH_2)_nNHSO_2-,\ -\underset{\underset{R_{19}}{|}}{N}-,\ -\underset{\underset{O}{||}}{C}O-\!\!\left\langle\!\!\bigcirc\!\!\right\rangle\!\!-O\underset{\underset{O}{||}}{C}-,$$

$$-\underset{\underset{O}{||}}{C}NH-\!\!\left\langle\!\!\bigcirc\!\!\right\rangle\!\!-NH\underset{\underset{O}{||}}{C}-,\ -SO_2O-\!\!\left\langle\!\!\bigcirc\!\!\right\rangle\!\!-OSO_2-\ \text{or}$$

$$-SO_2NH-\!\!\left\langle\!\!\bigcirc\!\!\right\rangle\!\!-NHSO_2-$$

$R_{18}$ is hydrogen or alkyl having 1 to 10 carbon atoms, $R_{19}$ and $R_{20}$ are hydrogen or alkyl having 1 to 5 carbon atoms, which is unsubstituted or substituted by halogen, hydroxyl or acyl having 2 to 5 carbon atoms, m is an integer from 1 to 20, n is an integer from 2 to 20 and $R_7$, $R_8$, $R_9$, $R_{10}$, $X_5$, $X_6$, $X_7$, $X_8$ and r are as defined.

Further preferred recording materials for colour photography are those which contain, as yellow couplers, compounds of the formula

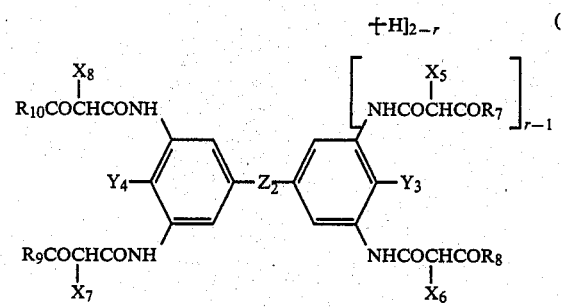

in which $Z_2$ is

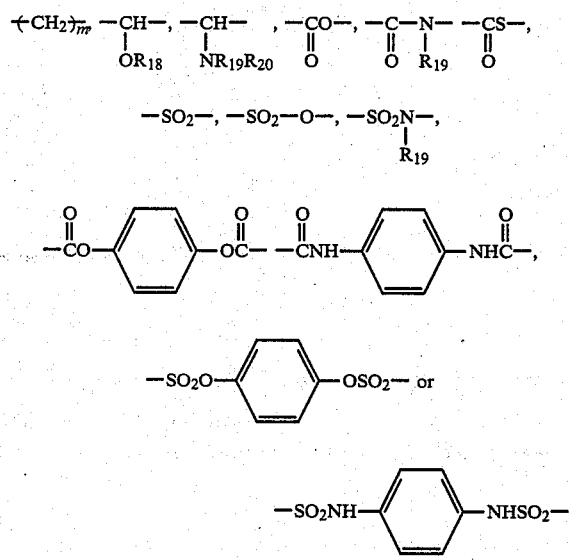

and $R_7$, $R_8$, $R_9$, $R_{10}$, $X_5$, $X_6$, $X_7$, $X_8$, $Y_3$, $Y_4$, $R_{18}$, $R_{19}$, $R_{20}$, m and r are as defined, or compounds of the formula

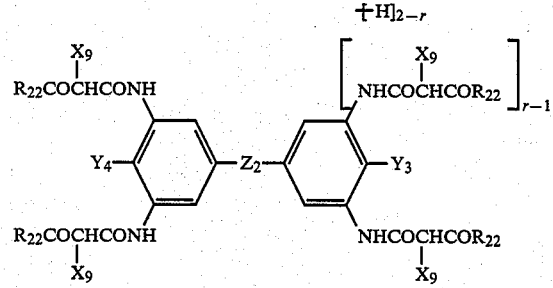

in which $R_{22}$ is straight-chain or branched alkyl having 3 to 10 carbon atoms, cyclopentyl, cyclohexyl, adamantyl, phenyl or phenyl substituted by chlorine or bromine, alkyl or alkoxy, each having 1 to 4 carbon atoms, or —O—(CH$_2$)$_r$—O—, $X_9$ is hydrogen, chlorine or a radical of the formulae

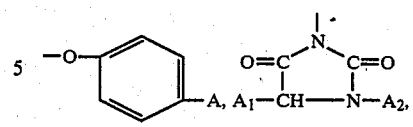

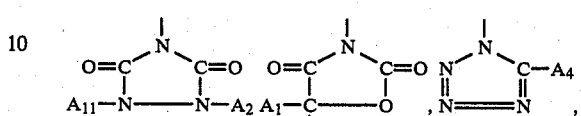

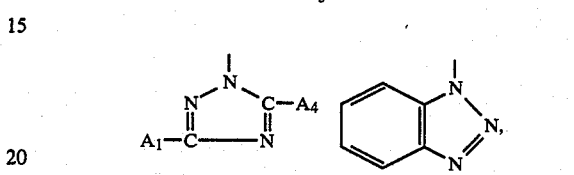

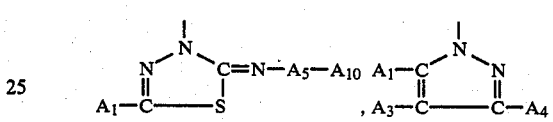

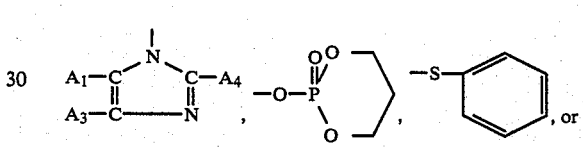

in which A is —COOH, —NO$_2$ or —COOR$_{21}$, in which $R_{21}$ is alkyl having 1 to 4 carbon atoms, or the radical of the formula

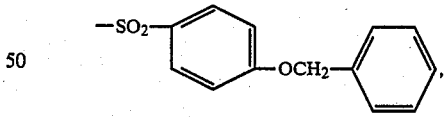

$A_1$ is hydrogen, alkyl having 1 to 18 carbon atoms, aralkyl, aryl, cycloalkyl having one to four cycloalkyl rings, alkoxy having 1 to 18 carbon atoms, aryloxy, alkylmercapto having 1 to 18 carbon atoms, arylmercapto, halogen, trifluoromethyl, cyano, —NH$_2$ or mono- or di-alkylamino in which the alkyl radicals each contain 1 to 18 carbon atoms,

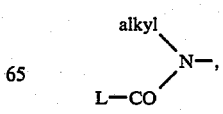

in which alkyl contains 1 to 5 carbon atoms,

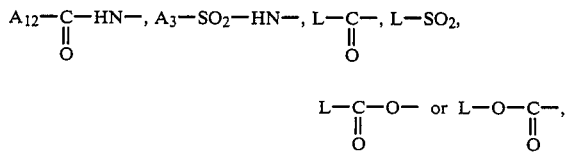

$$L-C-O- \text{ or } L-O-C-,$$

A₂ is straight-chain or branched alkyl having 1 to 18 carbon atoms, aralkyl, preferably benzyl or phenyl substituted by alkyl, alkoxy, halogen, NH₂, alkylamino, dialkylamino, acylamino, —COOH, carbalkoxy, carboxamido, sulfo, sulfonamido or alkylmercapto, A₃ is straight-chain or branched alkyl having 1 to 18 carbon atoms, which is unsubstituted or substituted by halogen, nitro, cyano, alkoxy or primary, secondary or tertiary amino groups, aralkyl or cycloalkyl having one to four cycloalkyl rings; aryl, which is unsubstituted or substituted by alkyl or alkoxy each having 1 to 4 carbon atoms, halogen, acylamino, —SO₃H, —COOH, sulfonamide or carboxamide, N-substituted or N,N-substituted sulfonamide or carboxamide, carboxylic acid ester, hydroxyl, nitro, primary, secondary or tertiary amine, mercapto, alkylmercapto, —SO₂—L or —CO—L; pyridyl, furyl, thienyl, perfluoroalkyl, acyl or dialkylamino, each having 1 to 5 carbon atoms in the alkyl moiety, alkoxy having 1 to 18 carbon atoms or phenoxy, A₄ is hydrogen, substituted or unsubstituted alkyl having 1 to 18 carbon atoms, cycloalkyl, cycloalkenyl, alkenyl, aryl, aralkyl, a heterocyclic radical, alkoxy, aryloxy, alkylmercapto, amino which is unsubstituted or substituted by alkyl, aryl or acyl, alkylsulfonyl, arylsulfonyl, acyloxy, aminosulfonyl, carboxamide, sulfonamide, alkyl carboxylate, nitro, cyano, halogen, substituted or unsubstituted ureido or substituted or unsubstituted aminosulfonylamino and A₅ is —CO— or —SO₂—, A₁₀ has the meaning defined for A₃ and is also hydrogen if A₅ is —CO—, A₁₁ is alkyl having 1 to 18 carbon atoms, which is unsubstituted or substituted by halogen, amino, cyano or alkoxy, or cycloalkyl, aryl or aralky, A₁₂ is hydrogen or has the meaning defined for A₃ and L is alkyl having 1 to 18 carbon atoms, which is unsubstituted or substituted by halogen, amino, cyano or alkoxy, or cycloalkyl, aryl, pyridyl, pyrimidyl, furyl or thienyl and Y₃, Y₄, Z₂ and r are as defined.

Finally, particularly preferred materials for colour photography are those which contain the yellow couplers of the formula

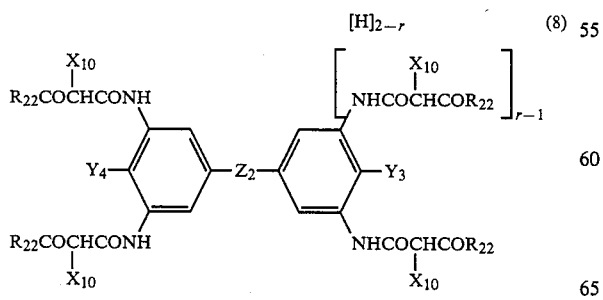

in which X₁₀ is hydrogen, chlorine or a radical of the formulae

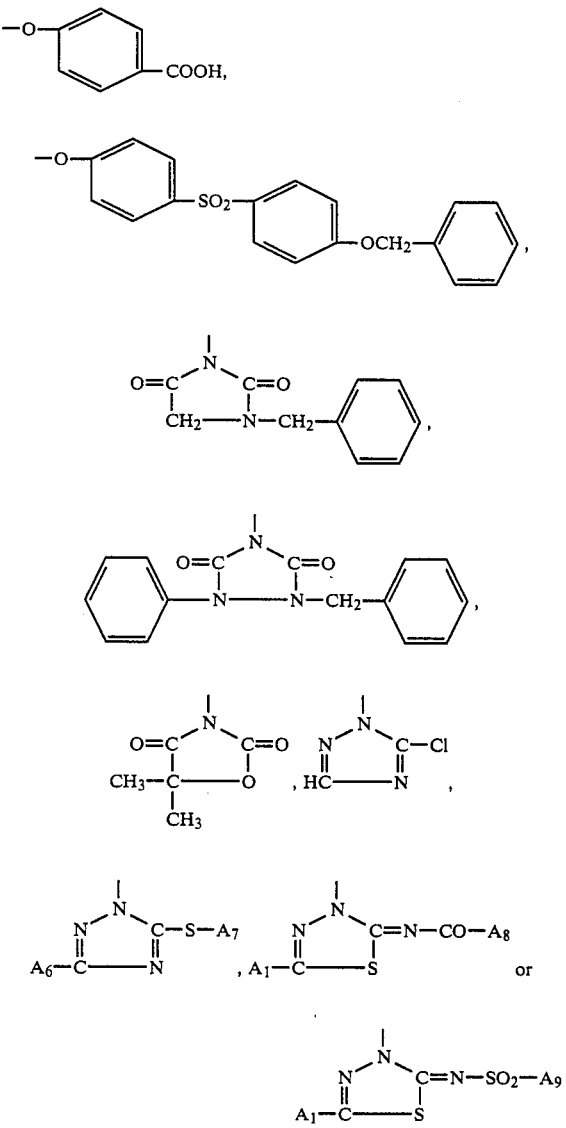

in which A₆ is hydrogen or alkyl having 1 to 4 carbon atoms, A₇ is alkyl having 1 to 12 carbon atoms, A₈ is straight-chain or branched alkyl having 1 to 18 carbon atoms,

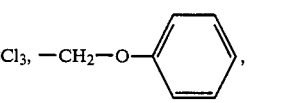

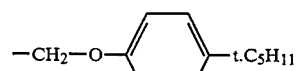

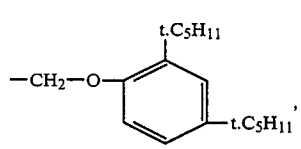

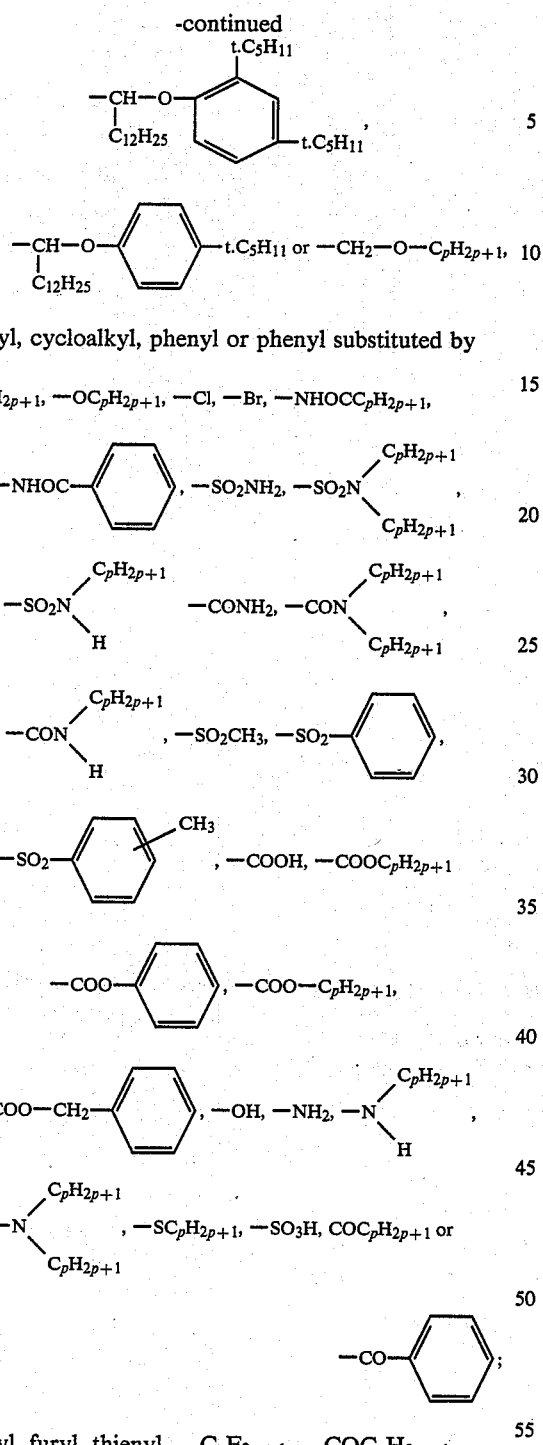

aralkyl, cycloalkyl, phenyl or phenyl substituted by $-C_pH_{2p+1}$, $-OC_pH_{2p+1}$, $-Cl$, $-Br$, $-NHOCC_pH_{2p+1}$, pyridyl, furyl, thienyl, $-C_pF_{2p+1}$, $-COC_pH_{2p+1}$,

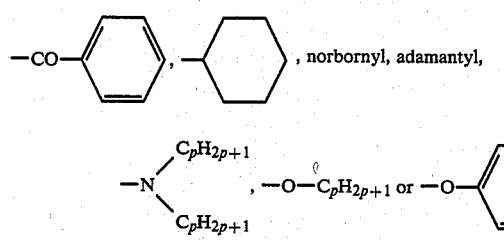, norbornyl, adamantyl, p is a number from 1 to 5 and $A_9$ is $-CH_3$,

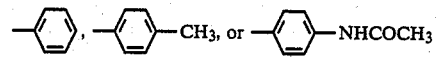

and $R_{22}$, $Y_3$, $Y_4$, $Z_2$, r and p are as defined.

Particularly suitable yellow couplers of the formula (8) are those of the formula

 (9)

and

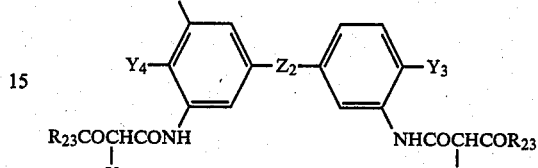 (10)

in which $R_{23}$ is tert.-alkyl having 4 to 8 carbon atoms and $X_{10}$, $Y_3$, $Y_4$ and $Z_2$ are as defined.

In particular, $R_{23}$ is tert.-butyl, 1,1,3,3-tetramethylbutyl, 1-methyl-1-ethylpentyl or 1,1-dimethylpropyl.

$Y_3$ and $Y_4$ are preferably chlorine or alkoxy or alkyl having 1 to 5 carbon atoms (especially methyl or methoxy). $Z_2$ is particularly preferentially $-COO-$, $-SO_2NH-$, $-SO_2-$ or especially $-CONH-$.

The yellow couplers of the formula (1) can be prepared, for example, by reducing tri- or tetra-nitro compounds of the formula

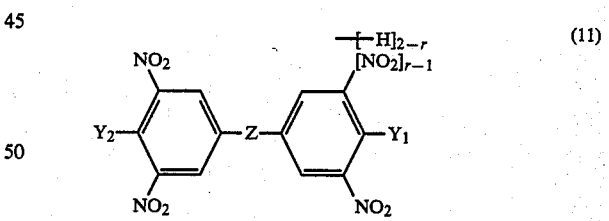 (11)

in which $Y_1$, $Y_2$, Z and r are as defined, to the corresponding amino compounds (triamines and tetramines) and then reacting these with suitable acyl compounds.

The compounds of the formula (11) are in some cases known from the literature or are prepared by generally known chemical methods, for example by reactions such as are indicated in the following equations;

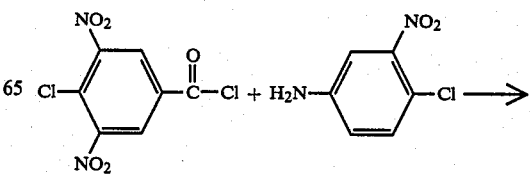

-continued

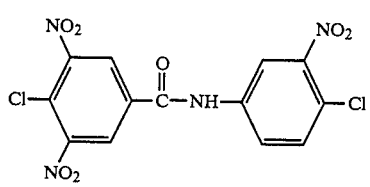

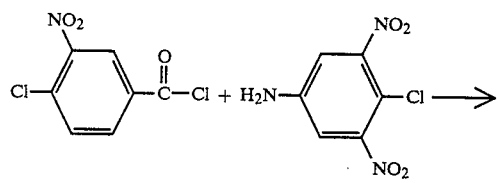

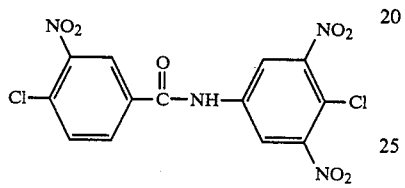

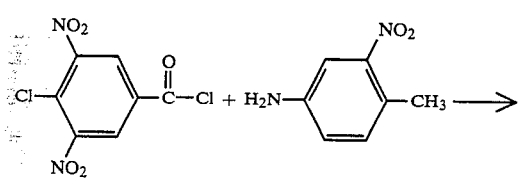

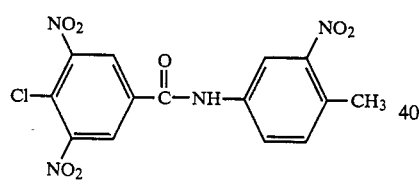

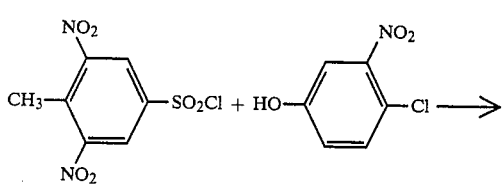

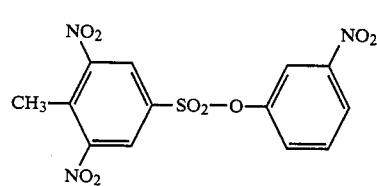

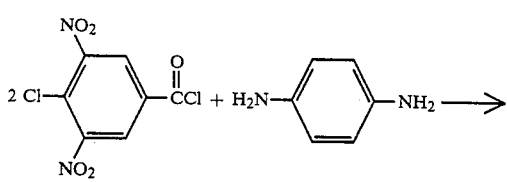

-continued

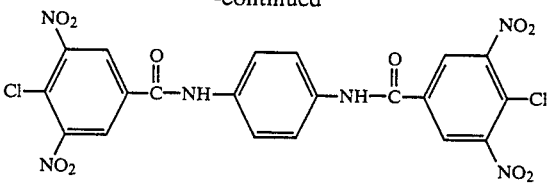

The dinitrobenzoic acids, dinitrosulfonic acids, dinitroamines or dinitrophenols of the formulae

 (12)

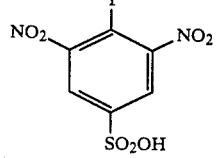 (13)

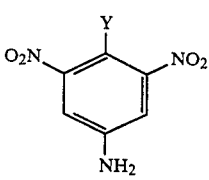 (14)

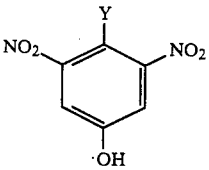 (15)

which are required as starting materials are known from the literature. They can be prepared by various methods, such as are described, for example, in Org. Synth. Coll. Vol. 4 364; Ann. 366, 95; Ann. 274, 349; J. Am. Chem. Soc. 49, 497 (1927); Ber. 42, 1729; Ber. 10; 1696 and Ber. 58, 1221.

Triamines and tetramines of the formula

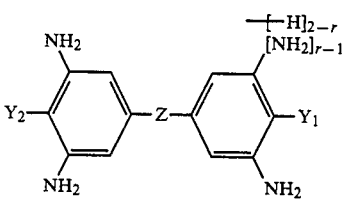 (16)

in which $Y_1$, $Y_2$, $Z$ and $r$ are as defined, are reacted with at least 3 or 4 mols of an ester of the formula

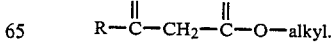 (17)

R has the meanings defined for $R_1$ to $R_4$. Esters of the formula (17) are known from the literature (for example U.S. Pat. Nos. 3,245,506 and 27,848, Org. Reactions, 1, 266 et seq.-Wiley New York and J.A.C.S. 70, 497 (1948)).

They are obtained, for example, by a condensation reaction of an acid chloride of the formula

  (18)

with the sodium compound of an alkyl acetoacetate and subsequent scission of the reaction product with a base (cf., for example, German Offenlegungsschriften 2,503,099 and 2,114,577, Org. Synth. Coll, Vol. II, 266 and J. Am. Chem. Soc. 67, 2197 (1945)).

The yellow couplers of the formula

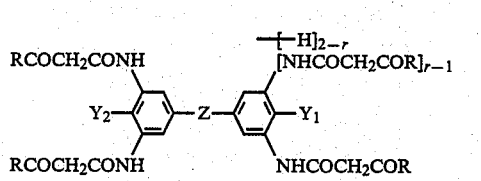 (19)

are obtained from the reaction of the keto-esters of the formula (17) with the triamines or tetramines of the formula (16).

The 3×4- or 4×4-equivalent couplers of the formula (19) obtained by the method of preparation described can be modified by replacing one hydrogen atom of the —CH$_2$—group by a halogen atom in a maner known per se. (cf., for example, German Offenlegungsschriften 2,263,875, 2,402,220 and 2,329,587 and U.S. Pat. No. 3,265,506).

These 3×2- or 4×2-equivalent couplers have the formula

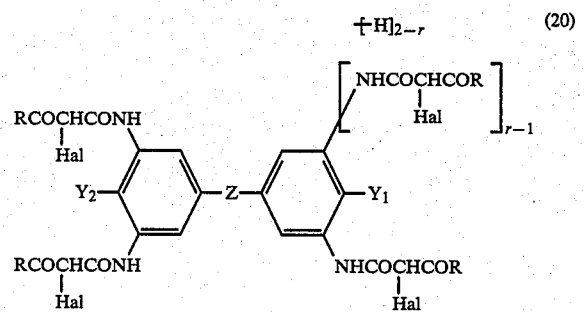 (20)

in which Hal is chlorine or bromine and the other symbols are as defined.

The two-equivalent couplers of the formula (20) can preferably be further reacted with salts of the formula

.

X is a radical which is detachable during the coupling reaction ($X_1$ to $X_4$) and $M^\oplus$ is a cation, for example Na, K or Ag. The yellow couplers of the formula (1) to (10) can be incorporated, in a known manner, in a silver halide emulsion containing gelatine or another binder.

They can be used on their own or as a mixture and in some cases even as a mixture with other couplers. The amount in which they are employed is between 50 and 300 g per mol of silver halide.

The silver halide emulsions used to prepare the photographic material according to the invention can contain, for example, silver bromide, silver iodide, silver chloride, silver chloride/bromide, silver iodide/bromide and silver chloride/iodide/bromide. Good results are also obtained when at least one photographic emulsion layer is used which contains silver chloride/iodide, silver iodide/bromide or silver chloride/iodide/bromide with an iodine content of 1 to 20 mol %.

The emulsions can be conventional negative emulsions or also direct positive emulsions. The emulsions can contain the customary additives, for example hardeners, sensitisers, stabilisers, wetting agents and antifogging agents.

Gelatine is preferably used as the binder for the photographic layers. However, this can be wholly or partly replaced by other naturally occurring or synthetic binders. Suitable naturally occurring binders are, for example, alginic acid and its derivatives, such as salts, esters or amides, cellulose derivatives, such as carboxymethylcellose, alkylcellulose, such as hydroxyethylcellulose, or starch and its derivatives, such as ethers or esters. Synthetic binders which can be used are, for example, acrylic resins, polyvinyl alcohol, partially saponified polyvinyl acetate or polyvinylpyrrolidone. Layer supports for the photographic material according to the invention are the sheets which are customarily used and suitable for this purpose, for example those made of cellulose nitrate, cellulose acetate, such as cellulose triacetate, polystyrene, polyesters, such as polyethylene terephthalate, polyolefins, such as polyethylene or polypropylene, and also papers, which can be coated, for example polyethylene-coated papers, and glass.

Corresponding application possibilities are described, for example, in U.S. Pat. Nos. 2,304,939, 2,304,940, 2,322,027, 2,284,879, 2,801,170, 2,801,171, 2,749,360 and 2,825,382. If desired, the couplers can also be employed in the developing bath.

The photographic developing baths in general contain an aromatic primary amine as the developer substance, preferably a p-phenylenediamine derivative, for example 4-amino-N,N-dimethylaniline, 4-amino-N,N-diethylaniline, 4-amino-3-methyl-N-methyl(ethyl)-N-(β-methylsulfonamidoethyl)-aniline or 4-amino-3-methyl-N-ethyl-N-(β-hydroxyethyl)-aniline, and also monomethyl-p-phenylenediamine, 2-amino-5-diethylaminotoluene, N-butyl-N-ω-sulfobutyl-p-phenylenediamine, N-ethyl-N-β-hydroxyethyl-p-phenylenediamine, N,N-bis-(β-hydroxyethyl)-p-phenylenediamine or 2-amino-5-(N-ethyl-N-β-hydroxyethylamino)toluene.

The couplers used according to the invention have a high coupling reactivity towards the oxidation product of the aromatic primary amine (developer), so that developing of the silver halide emulsion and formation of the dye proceed rapidly.

Furthermore, an outstanding reactivity and a good colour density are obtained with, at the same time, the use of the couplers according to the invention in a molar amount which is considerably reduced compared with that for known couplers. Since, at the same time, the amount of solvent for the coupler can be reduced, it is possible to reduce the total layer thickness of the emulsion layer.

If two-equivalent couplers are used, it is also possible to reduce the amount of silver halide. All of the measures lower the production costs for the photographic material.

The layer sensitive to blue light can be kept thinner and by this means the sharpness and the resolution of the resulting colour image are improved.

The coloured photographic image obtained with the yellow couplers employed according to the invention has excellent spectral absorption properties and also good resistance to light, heat and humidity and thus a sufficiently great stability to enable it to be stored for a prolonged period without any impairment.

In the following examples parts and percentages are by weight.

EXAMPLE 1

A solution of 25.6 g of N-[4-chloro-3,5-diaminobenzoyl]-4-chloro-3-aminoaniline and 53 g of methyl pivaloylacetate in 2 liters of xylene is heated at 140° C. for 5 hours. During this time the alcohol formed is continuously removed by distillation. After the reaction has ended, the reaction mixture is cooled in ice and the precipitate which has formed is filtered off and washed with hexane. 51.4 g of the compound of the formula

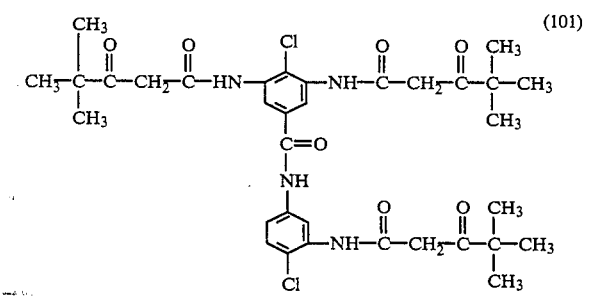

are obtained. Melting point: 165° to 168° C.

The other yellow couplers listed in Table I can also be prepared in an analogous manner.

TABLE I

Yellow couplers of the formula

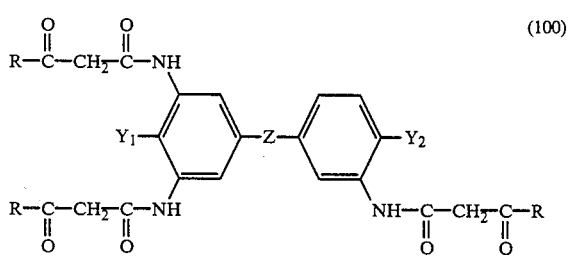

| No. | R | Z | $Y_1$ | $Y_2$ | Melting point °C. | $D_{max}$ |
|---|---|---|---|---|---|---|
| 101 | t-Butyl | —CONH— | Cl | Cl | 165–168 | 1.05 |
| 102 | t-Butyl | —SO$_2$—NH— | CH$_3$ | Cl | 142–146 | 1.10 |
| 103 | t-Butyl | —SO$_2$— | Cl | Cl | 100–102 | 1.26 |

TABLE I-continued

Yellow couplers of the formula

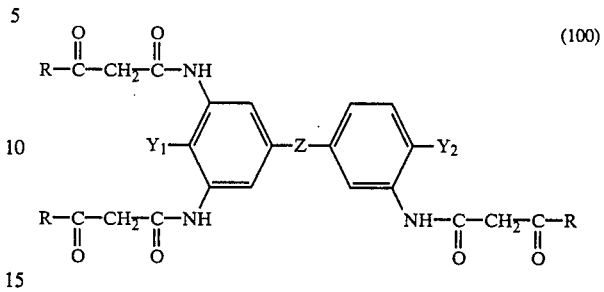

| No. | R | Z | $Y_1$ | $Y_2$ | Melting point °C. | $D_{max}$ |
|---|---|---|---|---|---|---|
| 104 | t-Butyl | —CONH— | Cl | CH$_3$ | 138–140 | 1.10 |

EXAMPLE 2

13 g of bromine are added slowly dropwise at 0° C. to a solution of 17.5 g of the coupler of the formula (101) in 1.5 liters of carbon tetrachloride. The ice bath is then removed and the mixture is stirred until it is at room temperature. The solution is washed with water until neutral and the organic phase is dried over sodium sulfate. After removing the solvent, a solid residue is obtained and this is recrystallised from a chloroform/hexane mixture. This yields 24.5 g of the compound of the formula

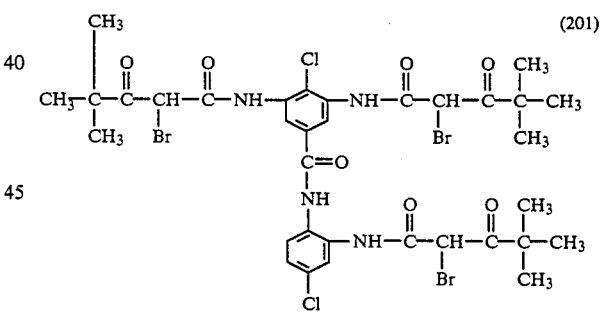

with a melting point of 140° to 142° C. (coupler No. 201 in Table II).

The other yellow couplers in Tables II and IV, in which X is Br, can be prepared in the same way.

EXAMPLE 3

A mixture of 5.9 g of the coupler of the formula (201), 1.10 g of potassium hydroxide and 4.76 g of 2-pivaloylamino-5-tert.-butyl-1,3,4-thiadiazole in 300 ml of dimethylformamide is stirred at room temperature for 10 hours. The mixture is poured into water and the precipitate which has formed is filtered off and recrystallised several times from a methanol/water mixture. This yields 2.9 g of the compound of the formula (202)
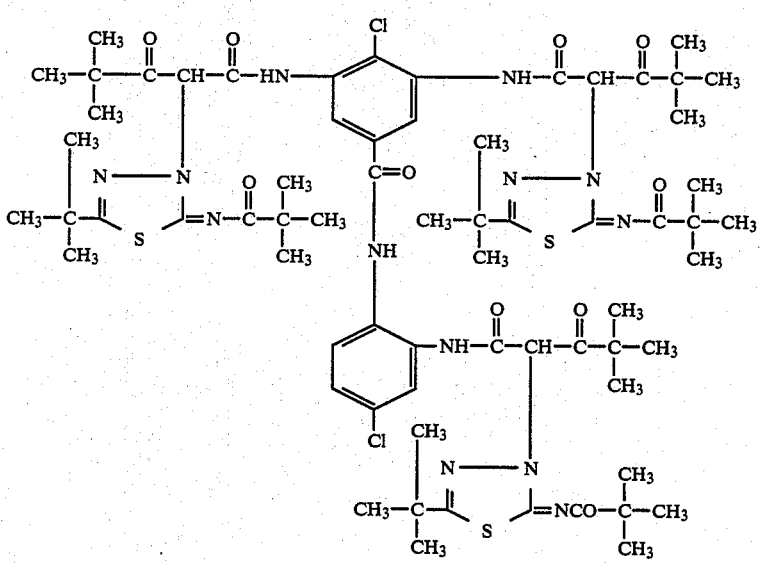
with a melting point of 163° to 166° C.
The other yellow couplers in Table II can also be prepared analogously.
TABLE II
Yellow couplers of the formula
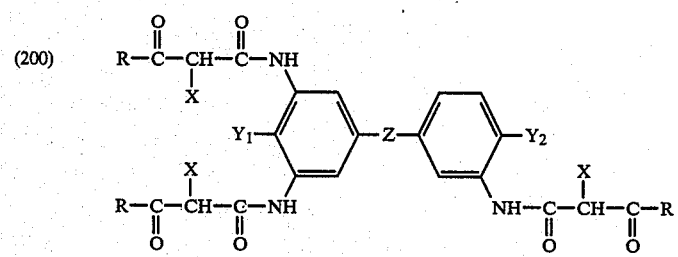
| No. | R | Z | $Y_1$ | $Y_2$ | X | Melting point °C. | $D_{max}$ |
|---|---|---|---|---|---|---|---|
| 201 | t-Butyl | —CONH— | Cl | Cl | Br | 140–142 | 1.29 |
| 202 | t-Butyl | —CONH— | Cl | Cl | | 162–163 | 1.41 |
| 203 | t-Butyl | —CONH— | Cl | Cl | | 160–165 | 1.53 |
| 204 | t-Butyl | —CONH— | Cl | Cl | | 192–195 | 1.28 |
| 205 | t-Butyl | —CONH— | Cl | Cl | | 162–165 | 1.15 |

TABLE II-continued

Yellow couplers of the formula (200) structure shown with R−CO−CH(X)−CO−NH− groups on a biphenyl system linked by Z, with substituents Y₁, Y₂

| No. | R | Z | Y₁ | Y₂ | X | Melting point °C | D$_{max}$ |
|-----|---|---|----|----|---|------------------|-----------|
| 206 | t-Butyl | —CONH— | Cl | Cl | (diphenyl-substituted acyl tosylamide structure) | 198–200 | 1.28 |
| 207 | t-Butyl | —SO₂—NH— | CH₃— | Cl | Cl | 125–126 | 1.28 |
| 208 | t-Butyl | —CONH— | Cl | Cl | (phenyl-thiadiazolyl pivaloylamide structure) | 179–180 | 1.23 |
| 209 | t-Butyl | —CONH— | Cl | Cl | (dimethyl oxazolidinedione structure) | 196–197 | 1.35 |
| 210 | t-Butyl | —SO₂NH— | CH₃— | Cl | (isopropyl-thiadiazolyl tosylamide structure) | 170–172 | 1.34 |
| 211 | t-Butyl | —SO₂— | Cl | Cl | Cl | 130–132 | 1.38 |
| 212 | t-Butyl | —SO₂— | Cl | Cl | (isopropyl-thiadiazolyl tosylamide structure) | 172–174 | 1.55 |
| 213 | t-Butyl | —SO₂— | Cl | Cl | (t-butyl-thiadiazolyl pivaloylamide structure) | 182–185 | 1.28 |
| 214 | t-Butyl | —CONH— | Cl | CH₃— | Cl | 116–118 | 1.10 |
| 215 | t-Butyl | —CONH— | Cl | CH₃— | (isopropyl-thiadiazolyl tosylamide structure) | 157–160 | 1.23 |

TABLE II-continued

Yellow couplers of the formula

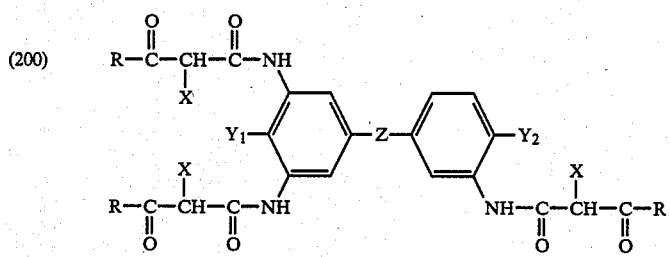
(200)

| No. | R | Z | $Y_1$ | $Y_2$ | X | Melting point °C. | $D_{max}$ |
|---|---|---|---|---|---|---|---|
| 216 | t-Butyl | —CONH— | Cl | $CH_3$— | (structure) | 162–165 | 1.26 |
| 217 | t-Butyl | —CONH— | Cl | $CH_3O$— | (structure) | 150–152 | 1.20 |
| 218 | t-Butyl | —CONH— | Cl | Cl | (structure) | 136–137 | 1.20 |

EXAMPLE 4

A solution of 13 g of N-[4-chloro-3,5-diaminobenzoyl]-4-chloro-3,5-diaminoaniline and 44 g of methyl pivaloylacetate in 2 liters of xylene is refluxed for 2 hours, the methanol formed being distilled off. After the reaction has ended, the xylene is evaporated off and the residue is recrystallised from a chloroform/hexane mixture and then from methanol. The compound of the formula

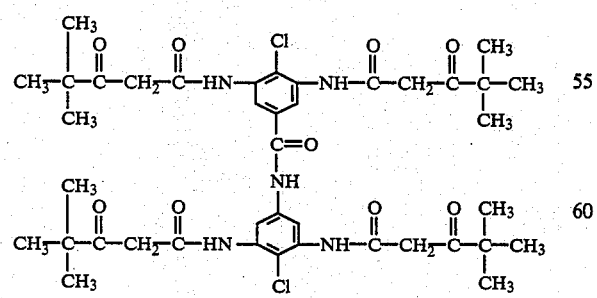

with a melting point of 150° to 155° C. is obtained. Yield: 68%.

The other yellow couplers in Table III can also be prepared analogously.

TABLE III

Yellow couplers of the formula (300)

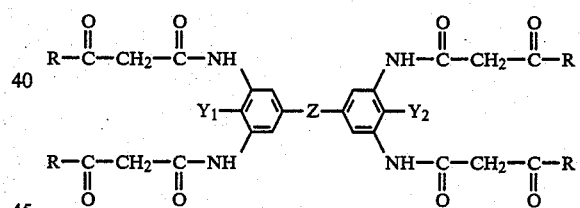

| No. | R | Z | $Y_1$ | $Y_2$ | Melting point °C. | $D_{max}$ |
|---|---|---|---|---|---|---|
| 301 | t-Butyl | —CONH— | Cl | Cl | 150–155 | 1.18 |
| 302 | t-Butyl | —$SO_2$— | Cl | Cl | 154–156 | 1.16 |

EXAMPLE 5

A mixture of 1.28 g of a coupler of the formula

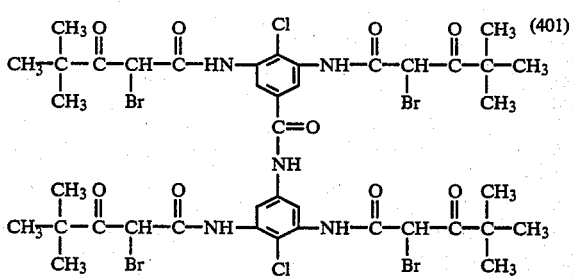
(401)

(prepared analogously to the process of Example 2) and 1.53 g of the potassium salt of 2-p-toluenesulfonylamino-5-isopropyl-1,3,4-thiadiazole in 400 ml of acetonitrile is stirred at room temperature for 6 hours. The mixture is poured into acidified water and the precipitate which has formed is filtered off and twice recrystallised from a chloroform/hexane mixture.

Compound (402) of Table IV is obtained as the product, which according to thin layer chromatography is a single compound.

Melting point: 168° to 170° C. Yield: 95%.

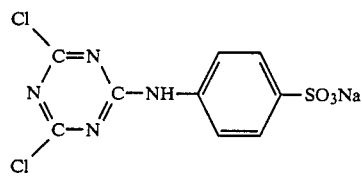

TABLE IV

Yellow couplers of the formula (400)

| No. | R | Z | $Y_1$ | $Y_2$ | X | Melting point °C. | $D_{max}$ |
|---|---|---|---|---|---|---|---|
| 401 | t-Butyl | —CONH— | Cl | Cl | Br | 139–144 | 1.29 |
| 402 | t-Butyl | —CONH— | Cl | Cl | (thiadiazole-N-SO₂-tolyl substituent) | 165–170 | 1.62 |
| 403 | t-Butyl | —CONH— | Cl | Cl | (thiadiazole-N-C(O)-C(CH₃)₃ substituent) | 175–177 | 1.30 |
| 404 | t-Butyl | —CONH— | Cl | Cl | Cl | 150–153 | 1.10 |

Use Example

EXAMPLE 6

Coupler emulsion 0.033 mmol of the yellow coupler of the formula (203) is dissolved in 2.0 ml of tricresyl phosphate/methylene chloride (1:9). The methylene chloride is evaporated off, 6.6 ml of 6% gelatine solution, 1.2 ml of water and 2.0 ml of an 8% aqueous solution of sodium isopropylnaphthalenesulfonate are added, the pH value of the mixture is adjusted to 6.5 and the mixture is emulsified for 5 minutes with the aid of an ultrasonic device with an output of 100 Watts.

Coating 2.5 ml of the coupler emulsion, freshly exposed to ultrasonic waves, 1.6 ml of a silver bromide emulsion which has a pH of 6.5 and contains 0.7% of silver and 6.0% of gelatine, 1.0 ml of a 1% aqueous solution of the hardener of the formula and 5.0 ml of water are mixed together and coated, at 40° C., onto a subbed 13 cm×18 cm glass plate.

After the mixture has solidified at 10° C., the plate is dried in a circulating air drying cabinet at room temperature.

Photographic exposure and processing

A strip cut to 4.0 cm×6.5 m is exposed, at 500 Lux/cm², under a step wedge for 6 seconds and then treated at 24° C. as follows:

| | Minutes |
|---|---|
| 1. Colour development | 5 |
| 2. Washing | 5 |
| 3. First fixing | 2 |
| 4. Washing | 2 |
| 5. Silver bleaching | 4 |
| 6. Washing | 2 |
| 7. Second fixing | 4 |
| 8. Washing | 10 |
| 9. Drying | 10 |

The processing solutions are of the following composition:

I. Colour developing solution (pH = 10.7)  10 mmol
   4-Amino-3-methyl-N—ethyl-N—α-
   (methylsulfonamido)-ethylaniline;

-continued

|  |  |
|---|---|
| 1½ H₂SO₄ · H₂O |  |
| Anhydrous sodium sulfide | 2.0 g |
| Potassium bromide | 0.5 g |
| Potassium carbonate | 40.0 g |
| Benzyl alcohol | 10.0 g |
| Water to make up to | 1000 ml |
| II. Fixing solution (pH = 4.5) |  |
| Sodium thiosulfate · H₂O | 80.0 g |
| Anhydrous sodium sulfite | 5.0 g |
| Sodium borate (Borax) | 6.0 g |
| Potassium alum | 7.0 g |
| Acetic acid | 4.0 |
| Water to make up to | 1000 ml |
| III. Silver bleaching bath (pH = 7.2) |  |
| Potassium ferrioyanide (III) | 100.0 g |
| Boric acid | 10.0 g |
| Sodium borate (Borax) | 5.0 g |
| Water to make up to | 1000 ml |

A clear, sharp yellow wedge which has an absorption maximum at 446 nm and a maximum colour density of 1.53 is obtained.

Photographic materials can also be produced, and processed, in the same way with the other yellow couplers described in Examples 1 to 5, including the tables. The $D_{max}$ values listed in the tables are then obtained.

What is claimed is:

1. A compound of the formula

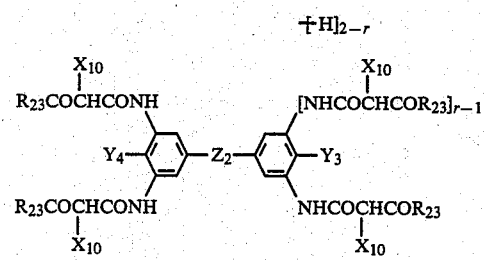

in which $X_{10}$ is hydrogen, chlorine or a radical of the formulae

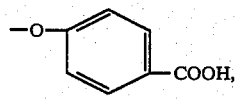

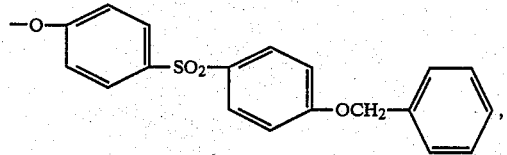

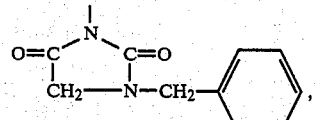

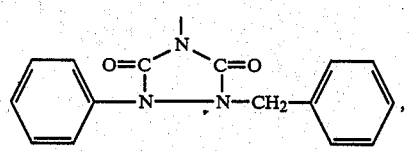

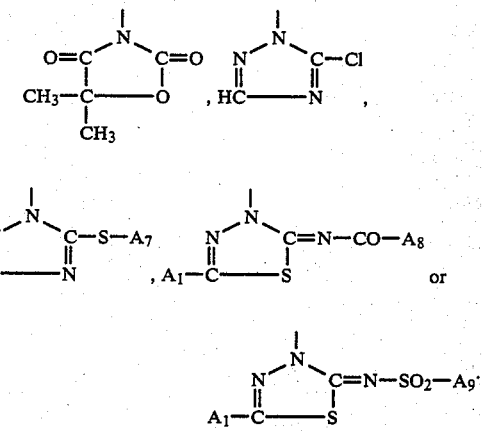

in which $A_6$ is hydrogen or alkyl having 1 to 4 carbon atoms, $A_7$ is alkyl having 1 to 12 carbon atoms, $A_8$ is straight-chain or branched alkyl having 1 to 18 carbon atoms,

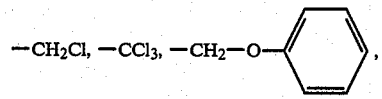

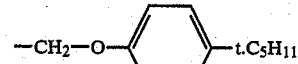

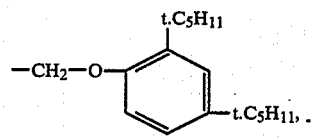

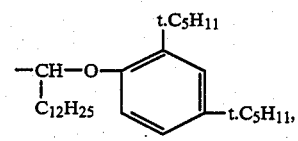

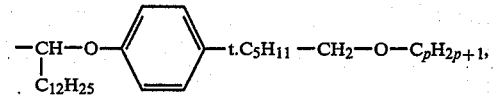

aralkyl, cycloalkyl, phenyl or phenyl substituted by

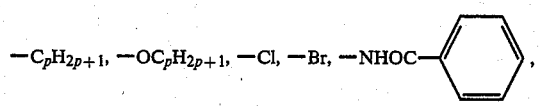

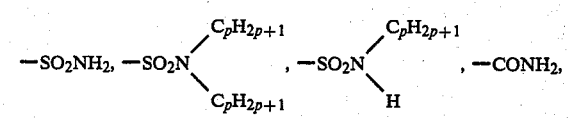

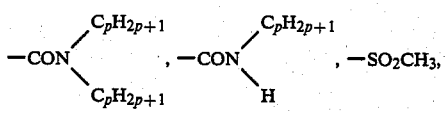

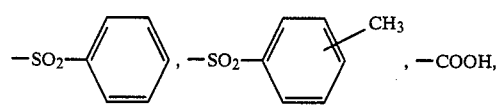, —COOH,
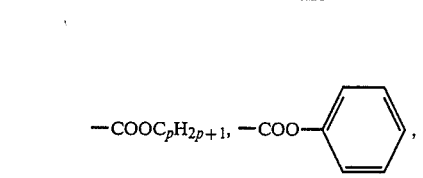
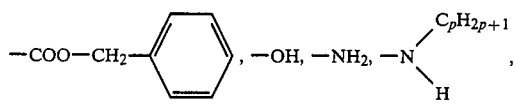
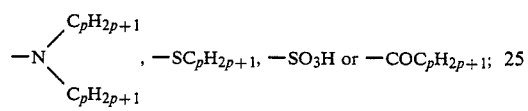
pyridyl, furyl, thienyl, —$C_pF_{2p+1}$,
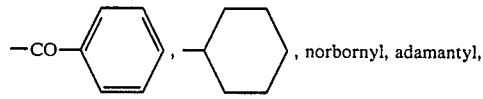, norbornyl, adamantyl,
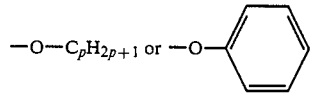
p is a number from 1 to 5 and $A_9$ is —$CH_3$,
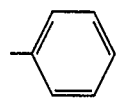
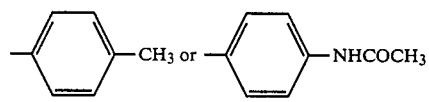
r is 1 or 2, $R_{23}$ is tert.-butyl, 1,1,3,3-tetramethylbutyl, 1-methyl-1-ethylpentyl or 1,1-dimethylpropyl, $Y_3$ and $Y_4$ are identical and are chlorine or alkyl or alkoxy each having 1 to 5 carbon atoms and $Z_2$ is —COO—, —$SO_2$— or —$SO_2NH$—.
* * * * *

UNITED STATES PATENT AND TRADEMARK OFFICE
CERTIFICATE OF CORRECTION

PATENT NO. : 4,568,752
DATED : February 4, 1986
INVENTOR(S) : Mario Fryberg

It is certified that error appears in the above-identified patent and that said Letters Patent is hereby corrected as shown below:

| | |
|---|---|
| Col. 1, line 43 | Correct spelling of "azomethine" |
| Col. 2, line 12 | After "postions" delete "which contain, per molecule, 3 or 4 reactive positions" (repeated twice) |
| Col. 11, line 44 | Correct spelling of "aralkyl" |
| Col. 28, line 67 | After "ethyl-N-" delete "α-" and substitute -- ß- -- |
| Col. 29, line 2 | Delete "sulfide" and substitute --sulfite-- |
| Col. 29, line 8 | Before "$H_2O$" insert --6-- |
| Col. 29, line 15 | Correct spelling of "ferricyanide" |

Signed and Sealed this

Twenty-fourth Day of June 1986

[SEAL]

Attest:

DONALD J. QUIGG

Attesting Officer      Commissioner of Patents and Trademarks